United States Patent [19]

Cuchiara

[11] 4,397,055
[45] Aug. 9, 1983

[54] REVERSABLE SHAFT WITH ROTARY AND SELECTIVE OSCILLATING MOTION

[76] Inventor: Samuel M. Cuchiara, 18609 LaGuardia, Rowland Hts., Calif. 91748

[21] Appl. No.: 198,608

[22] Filed: Oct. 20, 1980

[51] Int. Cl.³ .............................................. A46B 13/02
[52] U.S. Cl. ....................................... 15/22 R; 15/23; 74/22 R; 310/80; 320/2
[58] Field of Search ................... 15/22 R, 22 A, 22 C, 15/23, 24; 310/50, 80; 74/22 R, 22 A; 128/52, 56; 51/34 K

[56] References Cited

U.S. PATENT DOCUMENTS

| | | | |
|---|---|---|---|
| 2,484,471 | 10/1949 | Shinn | 74/22 R |
| 3,270,360 | 9/1966 | Kropp | 15/22 R |
| 3,661,018 | 5/1972 | Keefer | 15/22 R |
| 3,699,952 | 10/1972 | Waters et al. | 15/22 R X |
| 4,084,280 | 4/1978 | May | 15/22 R |

FOREIGN PATENT DOCUMENTS 961427  6/1964  United Kingdom ................... 15/23

*Primary Examiner*—Edward L. Roberts
*Attorney, Agent, or Firm*—Kenneth T. Theodore

[57] ABSTRACT

The apparatus is a rotary shaft mechanism having selective axial oscillation and reversable rotary motion, preferably in a battery powered toothbrush. Within such a toothbrush, the user of same can easily select either a clockwise or counter clockwise rotation of the toothbrush and if desired, an axial oscillation for either rotation. The selective combinations permit the toothbrush to effectively move food particles away from the gum line independent of it's location on the teeth and to polish the teeth with its oscillation motion.

3 Claims, 3 Drawing Figures

REVERSABLE SHAFT WITH ROTARY AND SELECTIVE OSCILLATING MOTION

BACKGROUND OF THE INVENTION

1. Field of the Invention

This invention relates to mechanisms which rotate a shaft with selective bi-directional rotary rotation and selectively an axial oscillation. Specifically, the invention is described in the foregoing specification as within the field of electrically operated toothbrushes.

2. Description of the Prior Art

Electrically powered toothbrushes have been known to those skilled in the art for some time. Dentists have long recognized that proper brushing of teeth requires that the tooth brush move food particles away from one's gum line and also polish one's teeth. The above rotary toothbrushes typically are A.C. powered and uni-directional. They therefore move food particles away from the gum line for only one-half of all teeth. The above rotary oscillation toothbrushes typically have a 45 degree —90 degree arc of travel about it's axis in one direction before it oscillates back. Thus the gum line is subjected to brushing away from and also toward same. The net effect is that the gum line is not subjected to the contineous brushing away from the gum line as favored by dentists.

Additionally, the latter toothbrush is powered by levers, gears and such mechanisms which are very prone to wear and greatly reduces the mechanical efficiency of the toothbrush.

An additional category of toothbrushes attemps to provide axial oscillations by the use of a vibrating motor or solenoid. These however have proved ineffective due to the small displacement of the motors/solenoids.

SUMMARY & OBJECTS OF THE INVENTION

The invention is an electrically powered toothbrush having bi-directional rotation plus the user option of selecting large axial displacement of the brush during rotation. Said toothbrush has an elongated housing within which is a rechargeable battery, secondary charging coil, reversable motor, electrical switch, slideable end cap and shafts/coupling means for rotational movement of the brush. A unique cam mechanism within the housing permits large axial displacement of the brush and can be engaged/disengaged by the user as desired.

An object of the invention is to provide an electrically powered toothbrush which rotates in either direction for cleaning the upper and lower teeth by brushing food particles away from the gum line.

Another object of the invention is to provide an axial oscillation to a brush for polishing the teeth.

Another object of the invention is to provide both rotary and axial oscillation to a toothbrush.

These and other objects and features of advantage will become more apparent after studying the discription of the preferred embodiment together with the appended drawings.

BRIEF DESCRIPTION OF THE DRAWINGS

FIG. 3 is a detail of the cam mechanism.

DESCRIPTION OF THE PREFERRED EMBODIMENT

While the preferred embodiment is illustrated and described below, it is to be understood that variations will be apparent to those skilled in the art without departing from the principles of the invention. Accordingly, the invention is not to be limited to the specific form described and illustrated but rather is to be limited only by a literal interpretation of the claims as appended herein.

Figure 1:
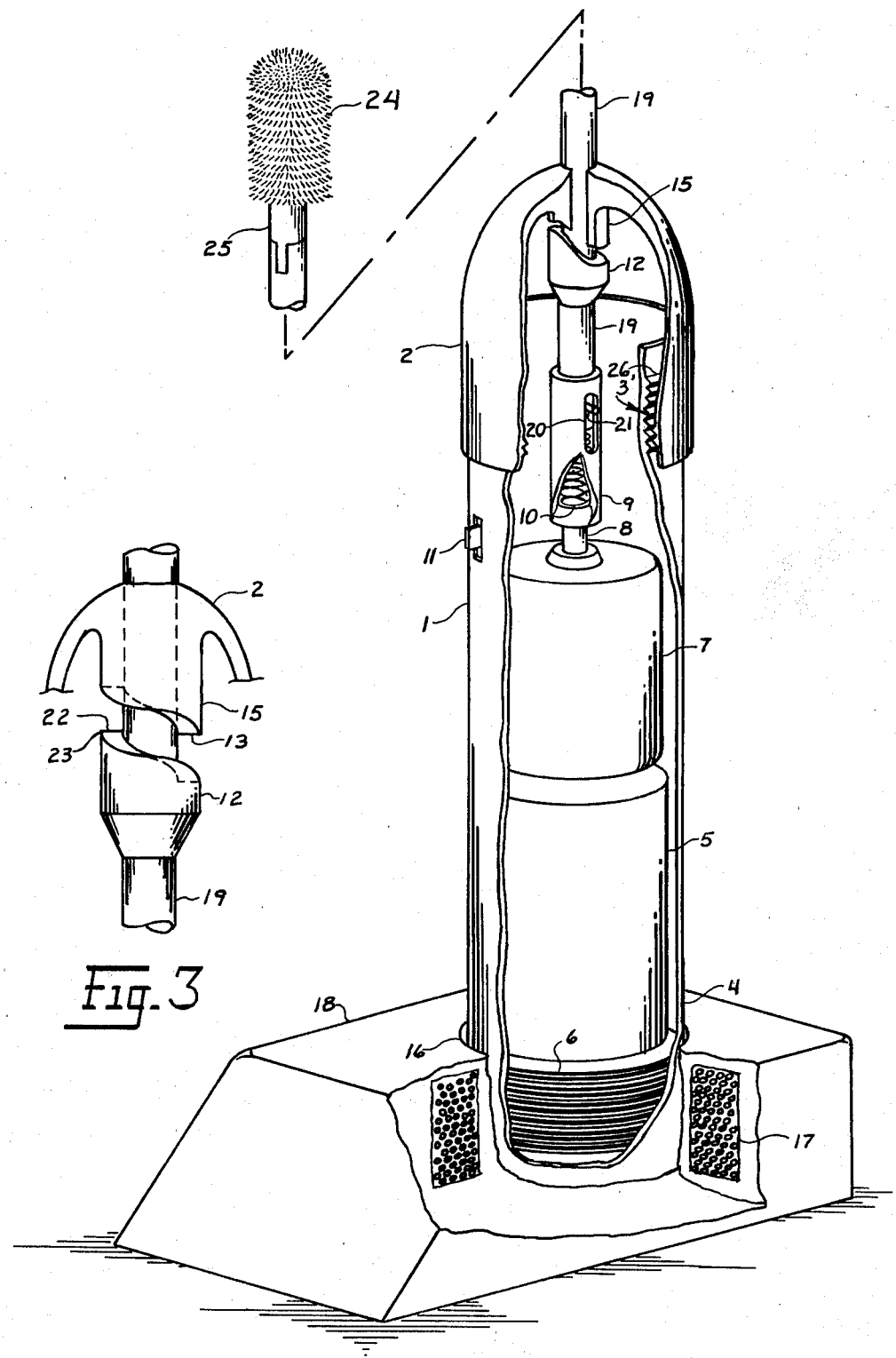
FIG. 1 is a sectional isometric view of the toothbrush illustrating the novel arrangement of the elements therein.

Referring to FIG. 1, a powered toothbrush is isometrically shown, illustrating the novel shaft arrangement with bi-directional rotary motion and selectively large displacement oscillation motion. The toothbrush has a tubular housing 1, a base end 4 and a forwardly facing slidable end cap 2. Within the end 4 is enclosed a secondary coil 6 electrically connected to a rechargeable battery 5. Axially disposed forward of and electrically connected to said battery 5 is reversable D.C. motor 7 with it's motor shaft 8 axially disposed forwardly. An electrical switch 11, mounted on the exterior of said housing 1, electrically connected said battery 5 and motor 7 for OFF-ON-REVERSE control of said motor 7.

Said end 4 is shown inserted within an aperture 16 located on a charger base 18 such that said toothbrush securely remains within and is stored in a vertical attitude. Within said base 18 and circumscribing said aperature 16 is a complimentary primary coil 17 such that the secondary coil 6 lies within the electrical induction field of the primary coil 17. In this manner, the secondary coil 6 is so energized to produce a current for recharging said battery 5. Electrical circuitry within said housing 1 prevents over-charging of the battery 5.

A hollow coupling means 9, having a suitable key engagement on one end thereof, engages said motor shaft 8 at said end. A pair of oppositely facing slots 20 axially orientated on the walls of said means 9 are positioned at the forward end of said means 9. The said forward end of said means 9 engages the rearwardly facing end of a brush holder shaft 19, axially and slidably disposed within said means 9. The said engagement can be of several methods such as a spline but the preferred embodiment utilizes a circular shaft 19 within means 9 for reasons obvious by further reading.

A pin 21, forceable pressed through the said end of shaft 19, radially projects outward through said slots 20. The pin 21 diameter is slightly smaller than the width of said slot 20 such that the pin 21 and shaft 19 freely traverse axially within said means 9 by a length limited to the length of said slots 20. Rotational movement of said means 9 imparts the same rotational movement to the pin 21 and thus the shaft 19, by the slots 20 acting against the pin 21.

A compression spring 10 is placed within said means 9 and forceably presses the shaft 19 axially forward. As will be obvious with further reading, said spring 10 returns said shaft 19 to it's most forward position during axial oscillations.

The shaft 19 axially extends through a rearwardly projecting shaft guide 15 which is intergal within a slidable end cap 2. A standard moisture proof seal is placed between said shaft 19 and guide 15 such that the shaft 19 is free to rotate and oscillate. The reaward facing end of said guide 15 has a helical screw shaped cam surface 13 wherein a radial line on the surface 13 is perpendicular to the shaft's axis. This surface 13 is more clearly illustrated in FIG. 3. Said surface 13 resembles a spiral staircase which rises for 180 degrees of rotation and then returns to its origin to complete 360 degrees of rotation. An axial cam 12 is located upon said shaft 19 adjacent to said surface 13 with a forwardly facing cam mating surface 22 co-dependant upon and slidably mates with said surface 13. The mating of said surfaces 13, 22 is accomplished by the continuous action of said spring 20. When the shaft 19 rotates said surface 22 upon the surface 13, said surface 22 is axially displaced rearward due to it's helical shape traversing upon a stationary helical shape, ie, the cam surface 13. As illustrated in FIG. 3, the contact between the two surfaces 13, 22 will alternate from a line contact to a bar contact. Of importance is that the contact upon surface 22 constantly moves and oscillates about it's apex 23. This greatly reduces the wear of surface 22 and considerable extends it's useful life. As will be obvious to those knowledgeable in the arts, the amount of axial displacement of said shaft 19 is dependent upon the height (or lead) of said surface 13 but in practice will be approximately one-quarter inch.

Material chosen for said surfaces 13, 22 will be those having a low surface friction with high structural strength to withstand expected bearing forces. Typically a nylon material is suitable, but does not preclude other materials.

Said cap 2 is joined to said housing 1 by a slidable joint 3 suitably waterproofed. Mating screw threads 26 within the joint 3 permit the cap 2 to be rotated such that it and the shaft guide 15 traverses forwardly a predetermined distance so that the rotating surface 22 will not engage or touch surface 13. As discussed previously, the length of said slot 20 limits the axial displacement of the shaft 19 and axial cam 12. By rotation of said cap 2, the oscillation mechanism is thus disengaged while retaining rotary motion of the shaft 19. This feature is independent of the shaft 19 direction of rotation.

Figure 2:
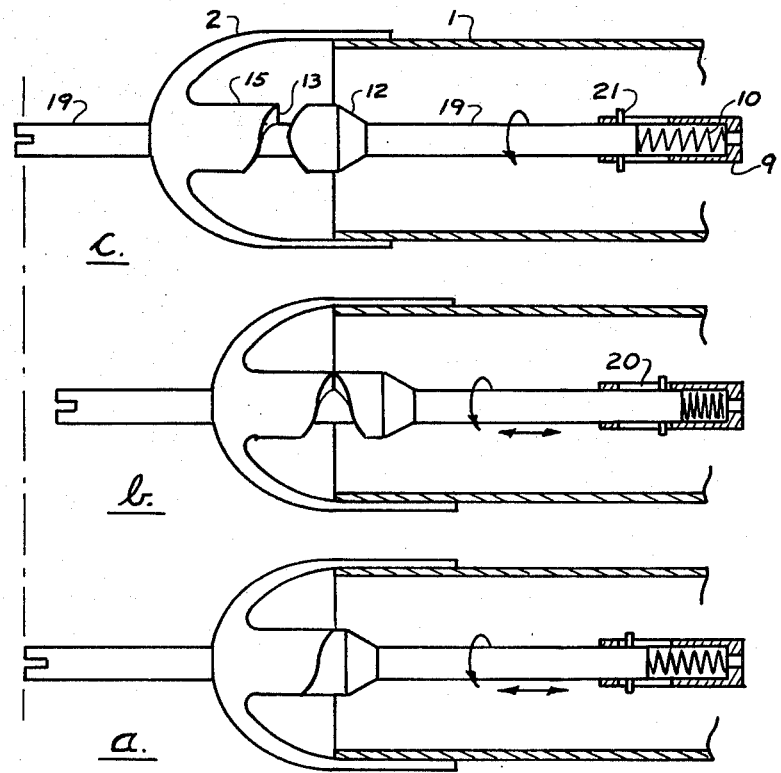
FIG. 2 is a three phase sectional view of the toothbrush's forward end illustrating the large axial displacement of the shaft.

FIG. 2 is three views (a,b & c) of the sequence of operation of the above oscillation mechanism. FIG. 2a illustrates the rotating shaft 19 at it's most forward position. FIG. 2b illustrates said shaft 19 rotated 180 degrees and the surface 22 (and thus the shaft 19) at it's most rearwardly or retracted position. FIG. 2c illustrates the oscillation mechanism disengaged by placing said cap 2 at it's most forward position. It is to be noted that the joint 3 contains indentations to lock said cap 2 in it's most forward and most rearward position such that the cap 2 will not traverse during use without a positive twisting effort to unlock same by the user.

Removably attached to the forward end of said shaft 19 is a brush rod 25 which has on it's end a toothbrush 24. Unlike all prior art, said brush 24 totally circumscribes the forward end of said rod 25. In this manner, the brush 24 is useable with a rotating movement and is bi-directional, thus capable of brushing away from the gum line at all teeth positions. The profile of said brush 24 is illustrated as cylindrical with a rounded end for the preferred embodiment but this is not to preclude other profiles which may be more advantageous.

Having thus described my invention, I claim:

1. An electrically powered toothbrush comprising:
   a tubular housing having a forward end;
   an electrical battery within said housing;
   an electrical motor with a motor shaft axially disposed within said housing and energized by said battery;
   an electrical switch on said housing for controlling said motor;
   an end cap, slidably attached to and enclosing said forward end, having a rearwardly projecting shaft guide with a helical shaped cam surface on it's most rearward end;
   a brush holder shaft traversably projecting forwardly through said end cap and slidably engaged to a coupling means, wherein said means is axially attached to said motor shaft;
   a compression spring within said means which forceably presses said shaft forwardly;
   and an axial cam on said brush holder shaft, located approximately near the cam surface, having a cam mating surface codependent with and simular to said cam surface;
   whereby rotation of said brush holder shaft rotates said cam mating surface upon the said cam surface thereby causing axial displacement of said brush holder shaft.

2. The toothbrush of claim 1 wherein,
   slots, having a predetermined length, are axially orientated on the wall of said means;
   a pin within the rearward end of said brush holder shaft radially projects through said slots whereby axial displacement of said shaft is limited by the length of said slots;
   a slidable joint with threads joins said end cap to said housing; and whereby moving said end cap forwardly disengages said surfaces such that only rotary motion is imparted to said shaft.

3. The toothbrush of claim 2 wherein,
   said battery is rechargable;
   said holder has a secondary coil electrically connected to said battery for inductance charging of said battery; and
   said motor is bi-directional.

* * * * *